US008153852B2

(12) United States Patent
Ellis et al.

(10) Patent No.: US 8,153,852 B2
(45) Date of Patent: Apr. 10, 2012

(54) PROCESS OF USING GERMANIUM ZEOLITE CATALYST FOR ALKANE AROMATIZATION

(75) Inventors: Paul E. Ellis, Sugar Land, TX (US); Gopalakrishnan G. Juttu, Glen Mills, PA (US); Alla K. Khanmamedova, Sugar Land, TX (US); Scott F. Mitchell, The Woodlands, TX (US); Scott A. Stevenson, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 421 days.

(21) Appl. No.: 12/387,179

(22) Filed: Apr. 29, 2009

(65) Prior Publication Data

US 2010/0280297 A1    Nov. 4, 2010

(51) Int. Cl.
*C07C 2/42* (2006.01)
(52) U.S. Cl. .......................................... 585/418; 585/419
(58) Field of Classification Search ................... 585/418, 585/419
See application file for complete search history.

(56) References Cited

U.S. PATENT DOCUMENTS

| | | | |
|---|---|---|---|
| 3,702,886 A | 11/1972 | Argauer et al. | |
| 4,443,326 A | 4/1984 | Field | |
| 5,052,561 A | 10/1991 | Miller et al. | |
| 5,182,012 A * | 1/1993 | Miller et al. | 208/137 |
| 5,376,259 A | 12/1994 | Kline et al. | |
| 5,397,454 A | 3/1995 | Zones et al. | |
| 6,160,191 A | 12/2000 | Smith et al. | |
| 6,323,381 B1 | 11/2001 | Nacamuli et al. | |
| 6,784,333 B2 * | 8/2004 | Juttu et al. | 585/419 |

OTHER PUBLICATIONS

H. Kosslick, et al.; Synthesis and Characterization of Ge-ZSM-5 Zeolites; Journal of Phys. Chem 1993, vol. 97, No. 21, pp. 5678-5684.
Scott M. Auerbach et al., "Handbook of Zeolite Science and Technology" 2003, pp. 42-45 and 129-164, Marcel Dekker, Inc. 270 Madison Avenue, New York, NY 10016, U.S.A., 42 pages.
Wayne J. Rohrbaugh et al., "Factors Affecting X-ray Diffraction Characteristics of Catalyst Materials" Characterization and Catalyst Development, An Interactive Approach; Mobil Research and Development Corporation, Paulsboro Research Laboratory, Paulsboro, NJ 08066-0480; Sep. 1988, Chapter 27, pp. 279-302., 27 pages.

* cited by examiner

*Primary Examiner* — Thuan Dinh Dang
(74) *Attorney, Agent, or Firm* — Cantor Colburn LLP

(57) ABSTRACT

This invention is for a catalyst for conversion of alkanes having two to six carbon atoms per molecule to aromatics. The catalyst is a MFI zeolite with a crystallite size of less than 15 microns with, in addition to silicon and aluminum, germanium as a framework element. Platinum is deposited on the zeolite. The zeolite may contain other optional tetravalent and trivalent elements in the zeolite framework. The catalyst is synthesized by preparing a zeolite containing aluminum, silicon, germanium and, optionally, other elements in the framework, calcining the zeolite and depositing platinum on the zeolite. The catalyst may be used for aromatization of alkanes, such as propane, to aromatics, such as benzene, toluene and xylenes.

19 Claims, 7 Drawing Sheets

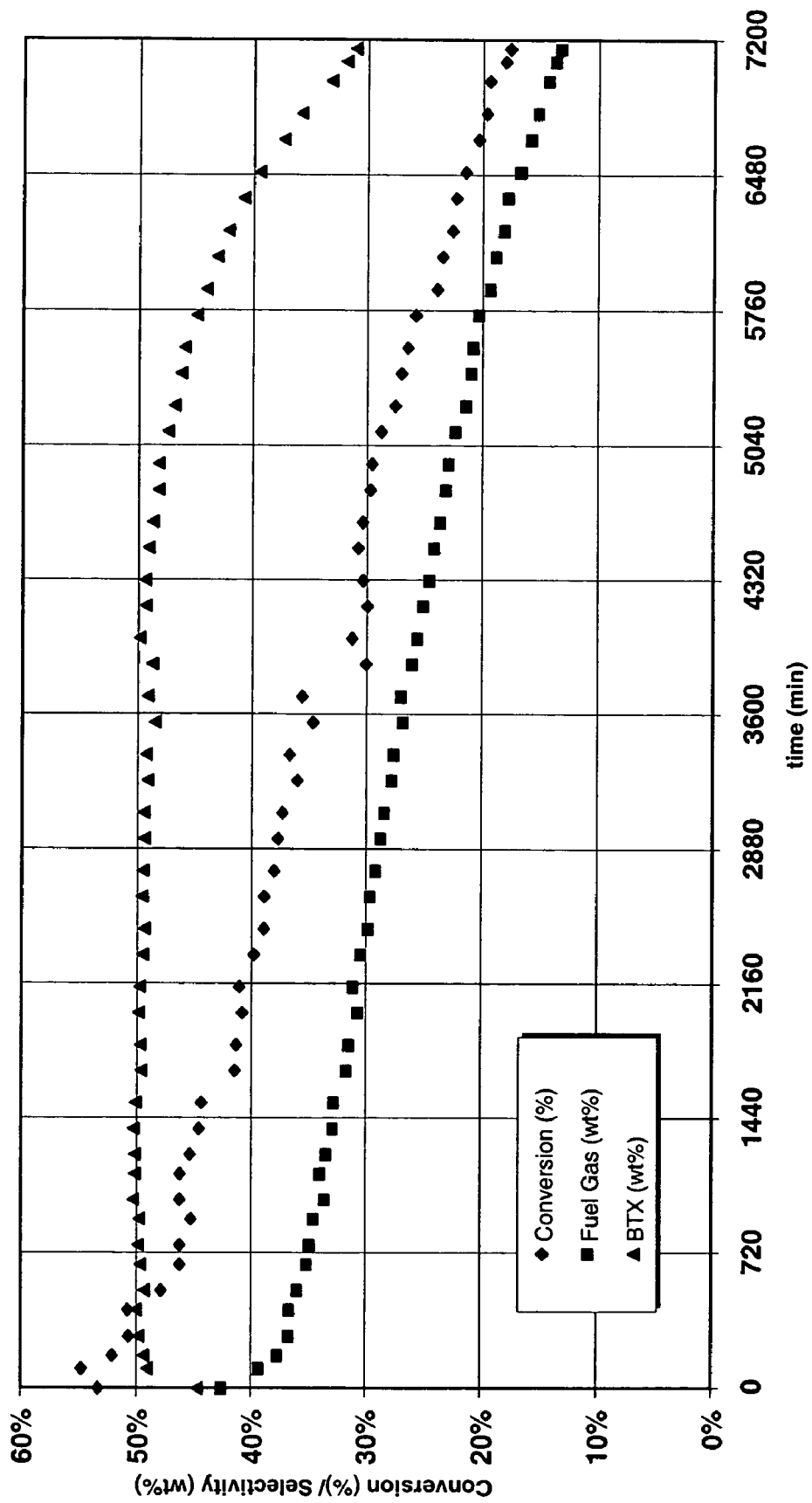
Figure 1: Catalyst 1

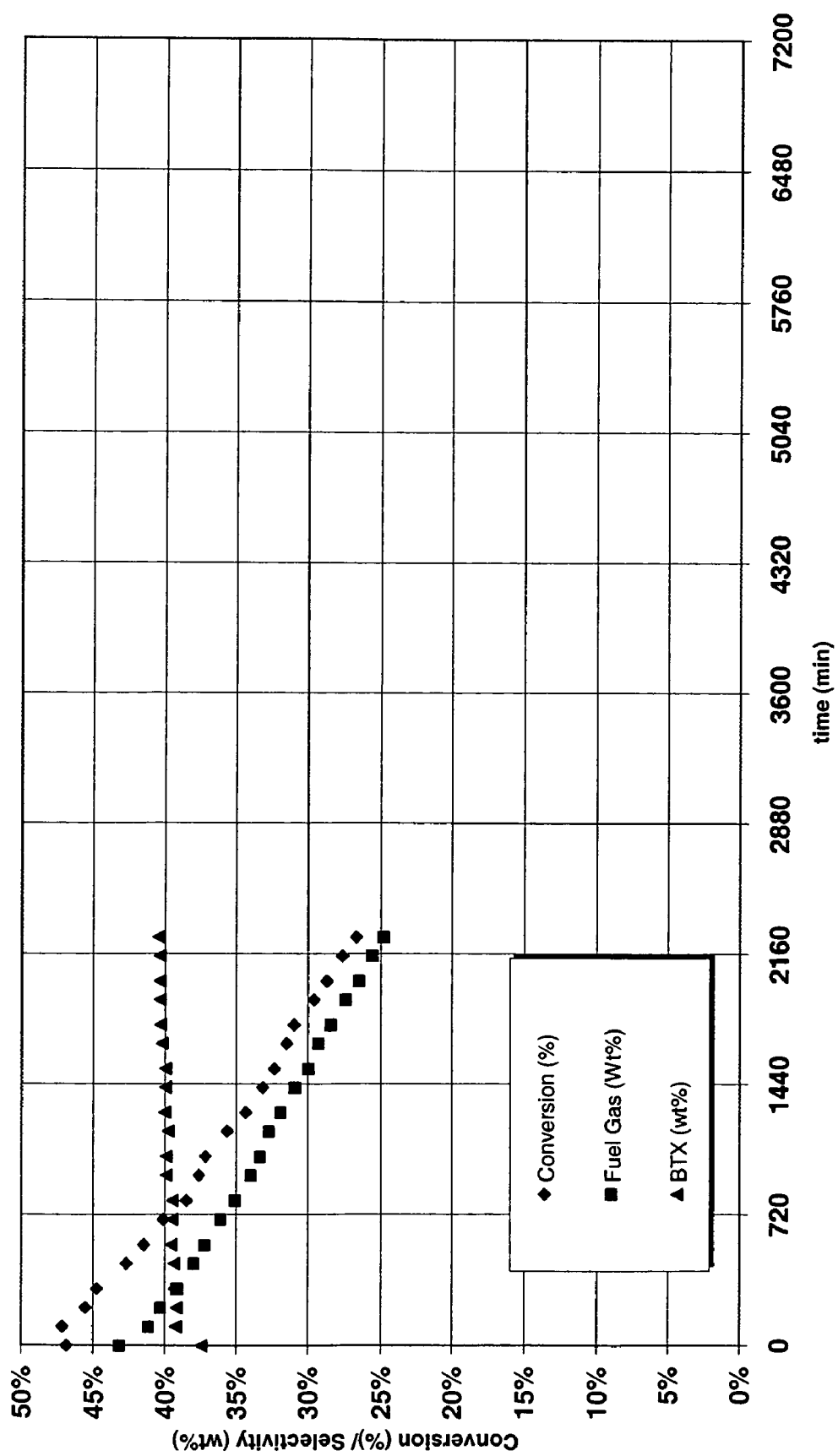
Figure 2: Catalyst 2

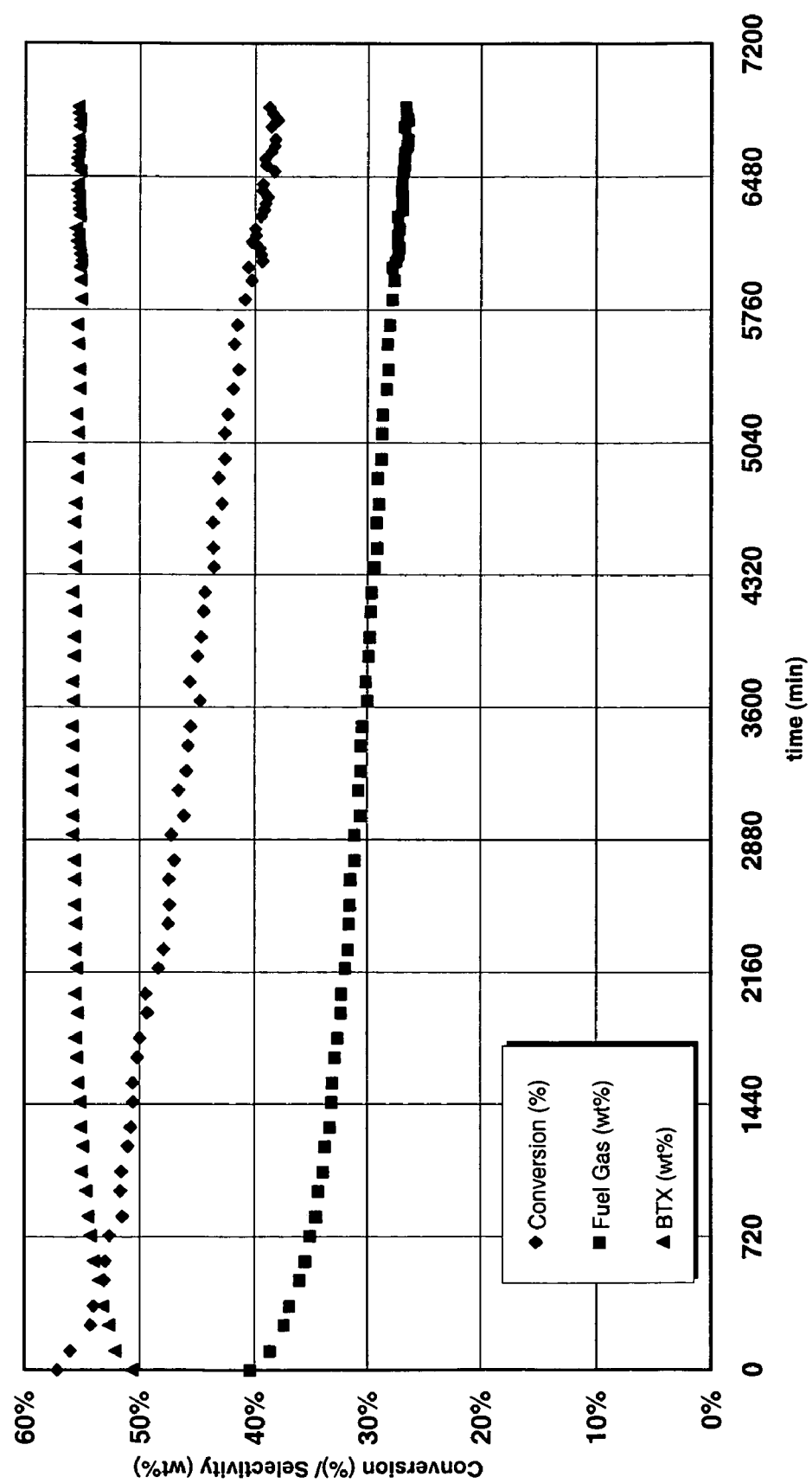

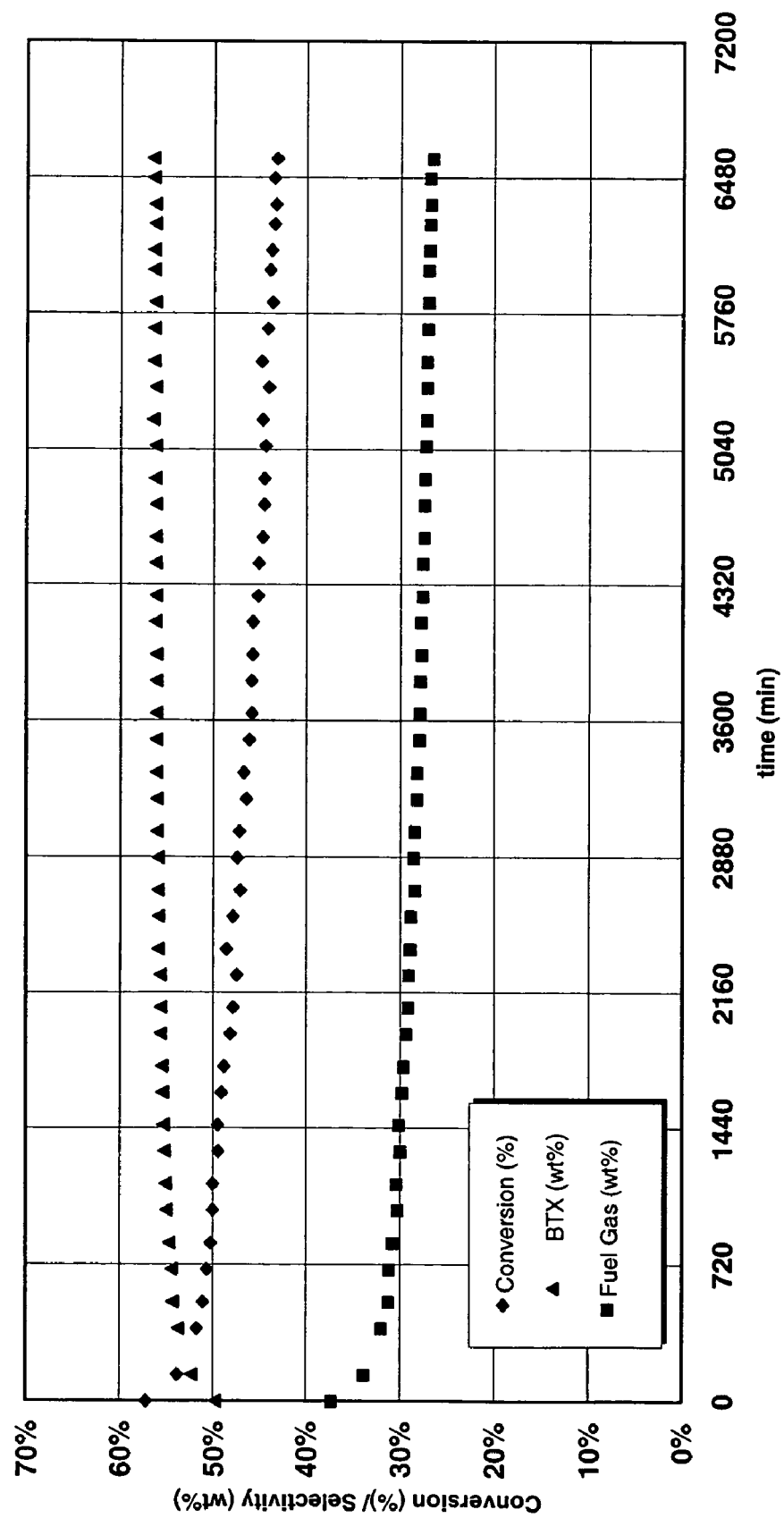
Figure 4: Catalyst 4

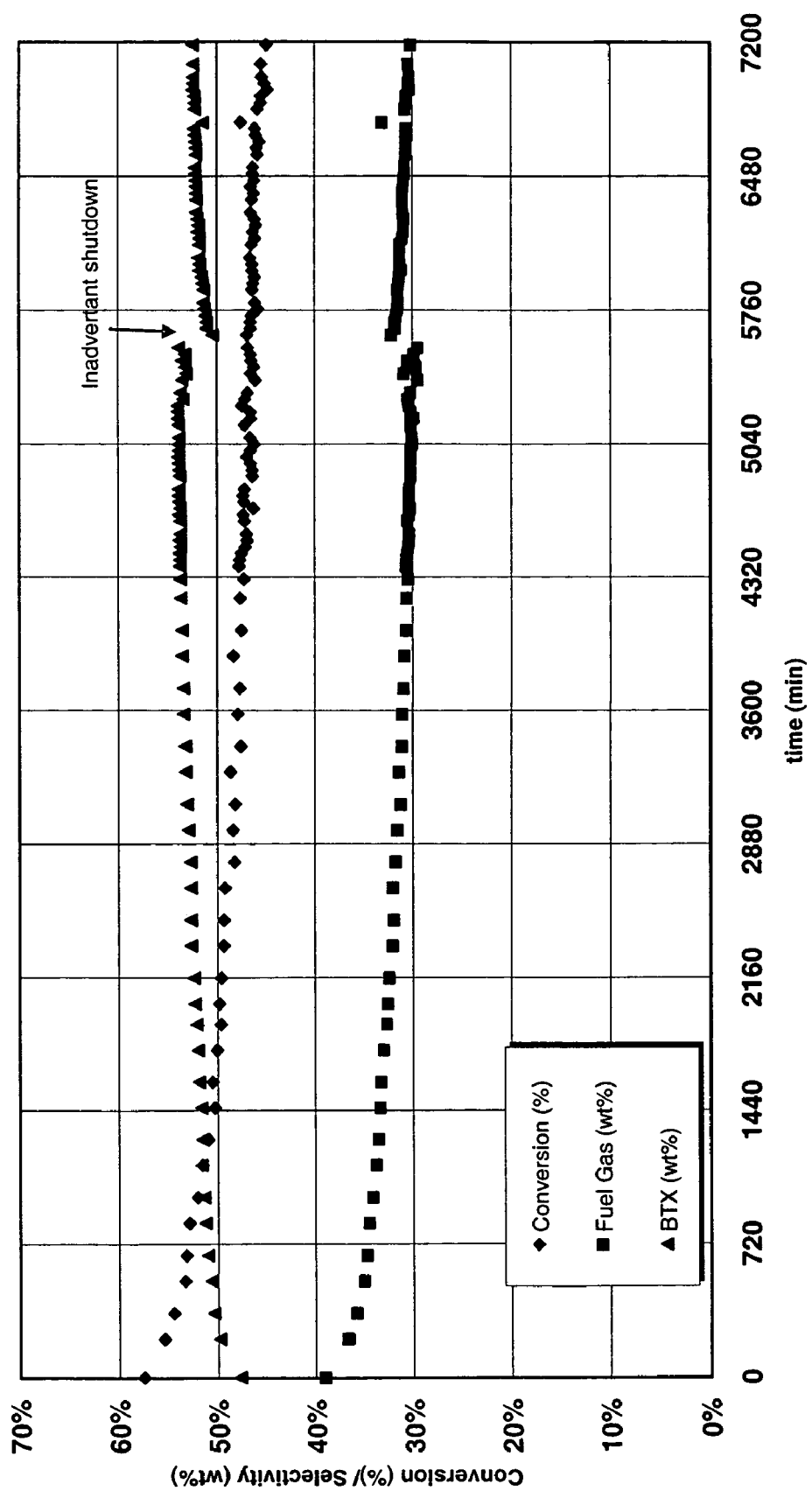

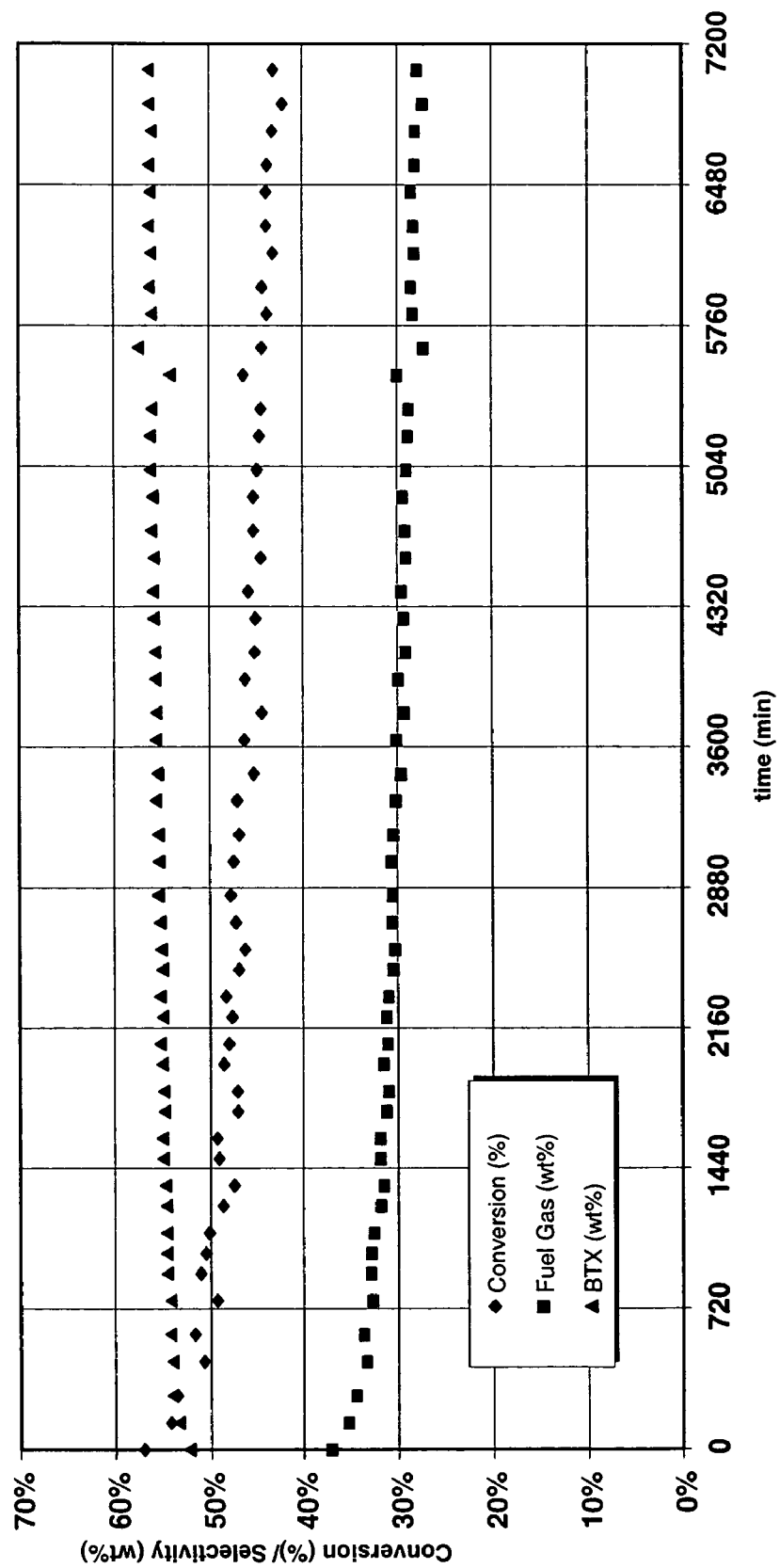
Figure 6: Catalyst 6

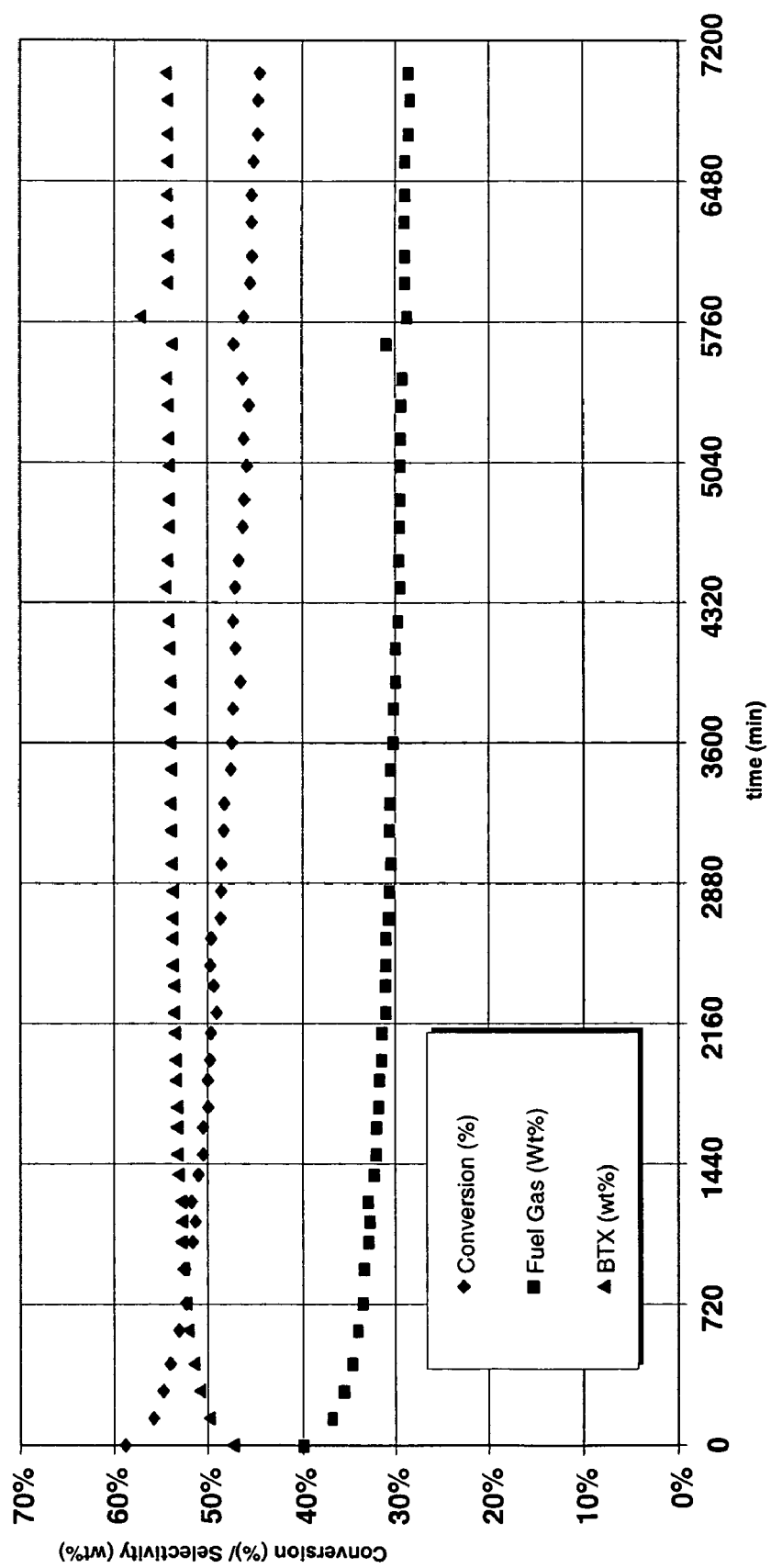
Figure 7: Catalyst 7

PROCESS OF USING GERMANIUM ZEOLITE CATALYST FOR ALKANE AROMATIZATION

BACKGROUND OF THE INVENTION

1. Field of the Invention

This invention relates to aromatization of alkanes having two to six carbon atoms per molecule, such as propane, to aromatics, such as benzene, toluene and xylenes, with a catalyst, such as a zeolite catalyst with germanium in the framework, e.g., a Ge-MFI-type zeolite having a certain crystallite size.

2. Description of the Prior Art

Zeolite is a crystalline hydrated aluminosilicate that may contain other metals in the framework of the zeolite crystal or deposited, exchanged or impregnated onto or into the porous zeolite. A method for preparing a zeolite comprises (a) preparing an aqueous mixture of silicon oxide and sources of oxides of aluminum; and (b) maintaining said aqueous mixture under crystallization conditions until crystals of zeolite form. In the crystalline structure there are pores and channels which may be interconnected. The dimensions and configuration of these pores and channels allow access by molecules of certain size. Zeolite by itself is known as an operative catalyst for many hydrocarbon conversion reactions but selectivity to a particular product may be low.

U.S. Pat. No. 4,443,326 discloses a hydrocarbon conversion process with a dehydrocyclization catalyst of a large pore zeolite, e.g., L zeolite, an alkaline earth metal, e.g., barium, and a Group VIII metal, e.g., platinum, to form a reformate which is contacted with a intermediate pore zeolite, e.g., ZSM-5, containing zinc. Crystal size of the L zeolite affected catalyst stability. Catalyst having at least 80% of the crystals larger than 1000 angstroms had longer run length than catalyst having substantially all of the crystals between 200 and 500 angstroms.

U.S. Pat. No. 5,397,454 discloses a novel composition of a crystalline zeolite SSZ-32. This patent also discloses that "[i]n general, lowering the crystallite size of a zeolite may lead to decreased shape selectivity. This has been demonstrated for ZSM-5 reactions involving aromatics as shown in J. Catalysis 99,327 (1986)."

U.S. Pat. No. 5,052,561 discloses a reforming catalyst with a high silica to alumina molar ratio (at least 500:1) and a small crystallite size (less than 10 microns). The reforming catalyst is a crystalline silicate that is substantially alumina-free on which a Group VIII metal, e.g., nickel, ruthenium, rhodium, palladium iridium or platinum, is finely dispersed.

U.S. Pat. No. 5,376,259 discloses a multistage process for producing aromatics, such as benzene, toluene, xylenes and ethylbenzene, from a hydrocarbon feed containing $C_6$-$C_8$ with a penultimate catalyst of platinum on alumina, silica/alumina or zeolite and a ultimate catalyst of platinum on an intermediate pore zeolite, such as ZSM-5, having crystallite size less than 10 microns, more preferably less than 5 microns, still more preferably less than 2 microns, and especially preferred less than 1 micron. The Examples disclosed average crystallite size of 0.4 and 0.3 micron.

U.S. Pat. No. 6,160,191 discloses "large" crystal zeolites as catalysts for hydrocarbon conversion processes, such as cracking of hydrocarbons, isomerization of alkyl aromatics, transalkylation of aromatics, disproportionation of alkylaromatics, alkylation of aromatics, reforming of naphtha to aromatics, conversion of paraffins and/or olefins to aromatics and conversion of oxygenate to hydrocarbon products. "Large" crystal zeolites have a mass mean diameter of from about 3 to about 10 microns and, more preferably, will have a mass mean diameter of from about 3 to about 6 microns. The zeolite may have a structure type of MEL, MTW, MTT, MFI, EUO, MFS, and TON and be a combination of trivalent elements, such as aluminum, gallium, zinc, iron, and/or boron and tetravalent elements such as silicon, tin, and/or germanium. The zeolite catalyst may be ion exchanged after calcination with a Group 1B to VIII Periodic Table metal, such as nickel, copper, zinc, palladium, platinum, calcium or rare earth metal.

U.S. Pat. No. 6,323,381 discloses a process for aromatizing a predominantly paraffinic feedstock with a substantially nonacidic catalyst of a Group VIII metal, such as platinum, on ZSM-5 having an average crystallite size of 0.5 to 2 microns.

It would be advantageous to have a zeolite-type catalyst which maintained relatively constant selectivity for conversion of lower alkanes, such as alkanes having two to six carbon atoms per molecule, to aromatics, such as benzene, toluene and xylene, over a period of time on stream.

SUMMARY OF THE INVENTION

The invention is for a process for converting a hydrocarbon feed containing alkanes having two to six carbon atoms per molecule to aromatics comprising contacting the hydrocarbon feed at aromatizing conditions with a catalyst comprising:

a) a MFI zeolite having a crystallite size of less than 15 microns and b) platinum deposited on the zeolite, wherein germanium is a framework element of the zeolite.

The catalyst is a germanium zeolite with a crystallite size of less than 15 microns on which a noble metal has been deposited. The catalyst is synthesized by preparing a zeolite containing aluminum, silicon and germanium, in the framework, depositing a noble metal, such as platinum, on the zeolite and calcining the zeolite. Examples of the zeolite structure are MFI, FAU, TON, MFL, VPI, MEL, AEL, AFI, MWW or MOR. A specific example of the zeolite structure is MFI or ZSM-5. One use for the catalyst is in a process for aromatization of alkanes by contacting the zeolite catalyst with at least one alkane at aromatization conditions and recovering the aromatic product.

BRIEF DESCRIPTION OF THE DRAWINGS

A more complete appreciation of the invention and many of the attendant advantages thereof will be readily understood by reference to the following detailed description when considered in connection with the accompanying drawings:

FIG. 1 is a graph of catalyst performance (conversion, selectivity and fuel gas production) v. time for Catalyst 1 (15-22 microns)

FIG. 2 is a graph of catalyst performance (conversion, selectivity and fuel gas production) v. time for Catalyst 2 (13-15 microns)

FIG. 3 is a graph of catalyst performance (conversion, selectivity and fuel gas production) v. time for Catalyst 3 (6-7 microns)

FIG. 4 is a graph of catalyst performance (conversion, selectivity and fuel gas production) v. time for Catalyst 4 (1.3-2 microns)

FIG. 5 is a graph of catalyst performance (conversion, selectivity and fuel gas production) v. time for Catalyst 5 (1-1.5 microns)

FIG. 6 is a graph of catalyst performance (conversion, selectivity and fuel gas production) v. time for Catalyst 6 (1-1.5 microns)

FIG. 7 is a graph of catalyst performance (conversion, selectivity and fuel gas production) v. time for Catalyst 7 (0.8-1 microns)

DETAILED DESCRIPTION OF THE INVENTION

The zeolite of the present invention can be prepared by any known method of preparing an aluminosilicate structure of aluminum and silicon. Zeolites are known to be crystallized silicates and include structures of $TO_4$ tetrahedra, which form a three dimensional network by sharing oxygen atoms where T represents tetravalent silicon and trivalent aluminum. Tetravalent elements, such as germanium, tin, lead, zirconium, titanium, vanadium or chromium, may be substituted for the silicon. Trivalent elements such as gallium, boron, indium, thallium or iron, may be substituted for the aluminum. These tetravalent and trivalent elements would be in the framework of the zeolite crystal. Other elements which may be in the framework of the zeolite crystal are zinc or phosphorus.

Zeolites generally crystallize from an aqueous solution. The typical technique for synthesizing zeolites comprises converting an amorphous gel to zeolite crystals by a hydrothermal process, employing a dissolution/recrystallization mechanism. The reaction medium also contains structuring agents which are incorporated in the microporous space of the zeolite network during crystallization, thus controlling the construction of the network and assisting to stabilize the structure through the interactions with the zeolite components.

Methods of preparation of a MFI zeolite can also be found in U.S. Pat. No. 3,702,886 and in J. Phys. Chem, vol. 97, p. 5678-5684 (1993), hereby incorporated by reference.

The noble metal is deposited on the zeolite by any known method of depositing a metal on a zeolite. Typical methods of depositing a noble metal on zeolite are ion exchange and impregnation. The noble metal is present preferably in the range from 0.05% to 3% by weight, more preferably in the range from 0.15% to 2% by weight and most preferably in the range from 0.15 to 1.5% by weight. The present invention may contain any noble metals, examples of which are palladium, silver, platinum and gold.

The catalyst may be bound by oxides of magnesium, aluminum, titanium, zirconium, thorium, silicon, boron and mixtures thereof. Preferably, the binder is an oxide of silicon (silica).

The catalyst preferably has average pore size preferably in the range from 5 angstroms to 100 angstroms, more preferably in the range from 5 angstroms to 50 angstroms and most preferably in the microporous range from 5 angstroms to 20 angstroms.

The catalyst may contain a reaction product, such as a sulfide of the noble metal, that is formed by contact of the noble metal element or compound deposited on the surface of the catalyst with a sulfur compound. Non-limiting examples of sulfur compounds are $H_2S$, $C_nH_{2n+2}S$ where n=1-20 or $C_nH_{2n+2}S_2$, where n=2-20. The sulfur compound may be added before or during the aromatization reactions of the alkanes, i.e., the catalyst may be pretreated with the sulfur compound or the sulfur compound may be introduced with the hydrocarbon feed when it contacts the catalyst during the aromatization process. One method of pretreating the catalyst is that, prior to contact with the hydrocarbonaceous feed, the catalyst is treated first with hydrogen, second with a sulfur compound; and then again with hydrogen. The amount of sulfur on the catalyst is preferably in the range of from 10 ppm to 0.1 wt. %.

The chemical formula of the catalyst may be represented as:

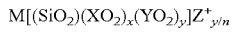

where M is a noble metal, such as platinum, X is a tetravalent element, Y is aluminum and, optionally, another trivalent element, Z is a cation with a valence of n, such as $H^+$, $Na^+$, $K^+$, $Rb^+$, $Cs^+$, $Ca^{2+}$, $Mg^{2+}$, $Sr^{2+}$ or $Ba^{2+}$, x varies from 0-0.15 and y is 0-0.125. According to the IUPAC recommendations, an example catalyst would be represented as:

The zeolite catalyst of the present invention is applicable to a variety of conversion processes which use catalysts to convert a hydrocarbonaceous feed, i.e., a feed containing hydrocarbons, all or in part. These processes and the useful range of process conditions are all well known in the art. One example of use of the zeolite catalyst of the present invention is for aromatization of alkanes to aromatics. A zeolite catalyst of the present invention, such as an MFI zeolite, may be used for the aromatization of alkanes having two to six carbon atoms per molecule to aromatics, such as benzene, toluene and xylenes.

One particular example of a hydrocarbon conversion process is dehydrocyclodimerization of light hydrocarbons to aromatics, e.g., CYCLAR™-type processing of $C_3$ alkane to aromatics, primarily benzene, toluene and xylenes. The CYCLAR™ process is described in the paper "CYCLAR: One Step Processing of LPG to Aromatics and Hydrogen," by R. F. Anderson, J. A. Johnson and J. R. Mowry presented at the AIChE Spring National Meeting, Houston, Tex., Mar. 24-28, 1985. The dehydrocyclodimerization process increases carbon chain length by oligomerization, promotes cyclization, and dehydrogenates cyclics to their respective aromatics. The process operates at a temperature of about 350° C. to 650° C. and a relatively low pressure of about 10 to 2000 kPa gauge.

Another particular example of a hydrocarbon conversion process using a zeolite catalyst of the present invention is dehydrocyclization of alkanes to aromatics, e.g., $C_{6+}$ alkanes to aromatics, primarily benzene, toluene and xylenes. The dehydrocyclization process promotes cyclization and dehydrogenates cyclics to their respective aromatics.

Another particular example of a hydrocarbon conversion process using a zeolite catalyst of the present invention is dehydrocyclodimerization of a $C_4$ raffinate stream containing butenes (n-, trans- and cis-) and butanes (n- and iso-) to aromatics, such as toluene and xylenes. A dehydrocyclodimerization process, such as the CYCLAR™ process described above, is applicable for converting a $C_4$ raffinate stream to aromatics.

The invention having been generally described, the following examples are given as particular embodiments of the invention and to demonstrate the practice and advantages thereof. It is understood that the examples are given by way of illustration and are not intended to limit the specification or the claims to follow in any manner.

Catalyst Preparation

All of the zeolites were prepared in a one liter stirred (300 rpm) autoclave. The following ratios were held constant:

| | |
|---|---|
| $SiO_2/Al_2O_3$ | 98.73 |
| $GeO_2/Al_2O_3$ | 6.59 |
| $TPAOH/SiO_2$ | 0.207 |

Chemicals used:
Colloidal silica LUDOX AS-40, 40%, Aldrich
Sodium hydroxide 50% aqua solution, Aldrich
Germanium (IV) oxide, $GeO_2$, 99.998%, Aldrich
Sodium aluminate (57 wt. % $Al_2O_3$; 35 wt. % $Na_2O$), Strem Chemicals
Tetrapropylammonium hydroxide, TPAOH, 40%, SACHEM
Acetic acid, 99.7%, Sigma-Aldrich The synthesis gels were aged from 1 to 24 hours, as indicated in Table 1, with stirring, after which the gels were acidified with acetic acid. The pH was measured after stirring for 10-15 minutes.

Catalyst 1

12.80 g of NaOH 50% aqua solution was mixed with 160 g of D.I. water. 6.69 g of $GeO_2$ was dissolved in this solution. Solution was introduced into 144 g of Ludox AS-40. Gel was formed and was stirred for 40 minutes. Solution of sodium aluminate (1.74 g) in 68 g of water was added to gel and gel was stirred for 5 minutes. Then 101.01 g of TPAOH was introduced into gel with stirring for 5 minutes. After that 107.6 g of water was added. Gel was stirred overnight. 60 g of acetic acid (50 wt. % solution in water) was added to gel to adjust pH (pH=7.76). Crystallization was made in 1 L stainless steel autoclave at 160° C. for 36 hours with stirring (300 rpm).

Catalyst 2

17.15 g of NaOH 50% aqua solution was mixed with 105 g of D.I. water. 7.43 g of $GeO_2$ was dissolved in this solution. Solution was introduced into 160 g of Ludox AS-40. Gel was formed and was stirred for 20 minutes. Sodium aluminate (1.93 g) solution in 75 g of water was added to gel with continuous stirring. Then 112.41 g of TPAOH was introduced into gel, and then 125 g of water was added. Gel was stirred overnight. 66.7 g of acetic acid solution in water (50/50 wt.) was added to gel (pH=8.90). Crystallization was made in 1 L stainless steel autoclave at 160° C. for 36 hours with stirring (300 rpm).

Catalyst 3

9.80 g of NaOH 50% aqua solution was diluted with 181 g of D.I. water and 7.43 g of $GeO_2$ was dissolved in this solution. Solution was introduced into 160 g of Ludox AS-40. Gel was formed and was stirred for about 20 minutes. Sodium aluminate (1.93 g) solution in 75 g of water was added to gel with continuous stirring. Then 112.21 g of TPAOH was introduced into gel, and then 125 g of water was added. Gel was stirred overnight. 47.0 g of acetic acid solution in water (50/50 wt.) was added to gel (pH=8.95). Crystallization was made in 1 L stainless steel autoclave at 160° C. for 36 hours with stirring (300 rpm).

Catalyst 4

8.82 g of NaOH 50% aqua solution was mixed with 160.6 g of D.I. water and 6.69 g of $GeO_2$ was dissolved in this solution. Solution was introduced into 144 g of Ludox AS-40. Gel was formed and stirred for 35 minutes. Sodium aluminate (1.74 g) solution in 68 g of water was added to gel with stirring for 10 minutes. Then 101.01 g of TPAOH was introduced into gel, and then 113 g of water was added. Gel was stirred overnight. 48.15 g of acetic acid solution in water (50/50 wt.) was added to gel (pH=7.26). Crystallization was made in 1 L stainless steel autoclave at 160° C. for 36 hours with stirring (300 rpm).

Catalyst 5

21 g of water and 32.03 g of TPAOH were added to Ludox AS-40 (45.67 g). Mixture was stirred for 20 minutes. Solution of 0.55 g of sodium aluminate in 18.73 g of water was added and mixture was stirred for 15 minutes. Then solution of 2.44 g of NaOH (50/50 wt. in water) and 2.12 g of $GeO_2$ in 54.7 g of water was added to the mixture and gel was stirred for 1 hour. After that 6.93 g of glacial acetic acid was added and pH measured after 20 minutes of stirring was 9.74. Crystallization was made in 300 mL stainless steel autoclave at 160° C. for 36 hours with stirring (300 rpm).

Catalyst 6

105 g of D.I. water and 112.21 g of TPAOH were added to 160.03 g of Ludox AS-40. Then solution of sodium aluminate (1.93 g) solution in 102 g of water was introduced. Mixture was stirred for 0.5 hour. After that solution of 9.14 g of NaOH (50/50 wt. in water) and 7.43 g of $GeO_2$ in 125 g of water was added to the mixture and gel was stirred overnight for 20 hours. Gel was acidified with 25.7 g of glacial acetic acid at pH=8.06. Crystallization was made in 1 L stainless steel autoclave at 160° C. for 36 hours with stirring (300 rpm).

Catalyst 7

100.09 g of D.I. water and 112.28 g of TPAOH were added to 160.01 g of Ludox AS-40. Mixture was stirred for 0.5 hour. Then solution of sodium aluminate (1.93 g) solution in 102 g of water was introduced. Mixture was stirred for 15 minutes. After that solution of 9.14 g of NaOH (50/50 wt. in water) and 7.43 g of $GeO_2$ in 130 g of water was added and gel was stirred for 1 hour. Gel was acidified with 25.7 g of glacial acetic acid at pH=9.23. Crystallization was made in 1 L stainless steel autoclave at 160° C. for 36 hours with stirring (300 rpm).

The contents of the autoclave were filtered and the solid material was washed with deionized water, dried at 90° C. overnight and calcined in air by increasing temperature from room temperature to 300° C. by 2° C./minute, holding temperature at 300° C. for three hours, increasing temperature from 300° C. to 500° C. by 2° C./minute, holding temperature at 500° C. for ten hours.

A sample of each zeolite was tested by X-ray diffraction (XRD) to determine uniformity of the sample and presence of amorphous material (represented by a halo in the XRD spectra). After confirming the absence of any significant amount of amorphous material, the sample was tested by scanning electron microscopy (SEM). Crystallite size was determined from the SEM micrographs of each catalyst sample at various magnifications. The results are shown in the Table below.

TABLE

| Catalyst | Aging (hr) | $OH^-/SiO_2$ | $Na_2O/SiO_2$ | NaOH (wt. %) | $Na/SiO_2$ | $H_2O/SiO_2$ | pH | Ge (wt. %) | Ge Inc. % | Crystallite size (microns) |
|---|---|---|---|---|---|---|---|---|---|---|
| 1 | 16 | 0.040 | 0.177 | 2.05 | 0.35 | 29.71 | 7.76 | 5.76 | 80 | 15-22 |
| 2 | 16 | 0.109 | 0.211 | 2.69 | 0.42 | 26.18 | 8.90 | 6.31 | 91 | 13-15 |
| 3 | 16 | 0.090 | 0.125 | 1.48 | 0.25 | 29.63 | 8.95 | 5.33 | 74 | 6-7 |
| 4 | 16 | 0.040 | 0.125 | 1.47 | 0.25 | 29.72 | 7.26 | 5.62 | 80 | 1.3-2 |
| 5 | 1 | 0.05 | 0.111 | 1.46 | 0.22 | 25.78 | 9.74 | 5.14 | 71 | 1-1.5 |
| 6 | 20 | 0.042 | 0.117 | 1.54 | 0.24 | 25.84 | 8.06 | 6.06 | 87 | 1-1.5 |
| 7 | 1 | 0.042 | 0.117 | 1.54 | 0.24 | 25.84 | 9.23 | 5.51 | 78 | 0.8-1 |

The zeolites were bound with silica (50 wt % zeolite, 50 wt % silica) and sized to 20-40 mesh particles. The catalyst was then converted into the $H^+$ form and $Pt^{2+}$ was deposited on the catalyst by ion exchange. A final calcination at 300° C. was performed before the catalyst was tested.

The catalyst was pretreated with $H_2$ and $H_2S$. Any excess $H_2S$ was stripped with $H_2$ again. The catalyst was tested at 500° C. at 33 psig with 1 $h^{-1}$ WHSV (weight hourly space velocity) propane. The results are shown in the figures.

The results show that a Pt/Ge-MFI zeolite having a crystallite size of less than about 15 microns can be used as a catalyst in a process for converting alkanes to aromatics, specifically propane to benzene, toluene and xylenes. Such a catalyst has improved propane conversion and BTX selectivity over a catalyst of a Pt/Ge-MFI zeolite having a crystallite size of about 15 microns or more. In more detailed analysis, the results show that a Pt/Ge-MFI zeolite having a crystallite size in the range from about 1 micron to about 7 microns, (Examples 3-7, FIGS. 3-7), can be used as a catalyst in a process for converting alkanes to aromatics, specifically propane to benzene, toluene and xylenes, with good conversion of alkane and good selectivity to aromatics and low fuel gas production relative to Pt/Ge-MFI zeolites having larger crystallite size (Examples 1 and 2, FIGS. 1 and 2). The results show that a Pt/Ge-MFI zeolite having a crystallite size of about 1.5 to about 2 microns has the good selectivity to benzene, toluene, and xylenes (Example 4, FIG. 4).

Zeolites below about 0.2 micron, e.g., in the range of about 0.1 to about 0.3 micron, are hard to filter and are not practical for use as catalyst, so one embodiment of the catalyst is a Pt/Ge-MFI zeolite having a crystallite size of greater than about 0.2 micron. Another embodiment of the catalyst is a Pt/Ge-MFI zeolite having a crystallite size of about 1 to about 7 microns. Another embodiment of the catalyst is a Pt/Ge-MFI zeolite having a crystallite size of about 1 to about 4 microns. Another embodiment of the catalyst is a Pt/Ge-MFI zeolite having a crystallite size of about 1.5 to about 2 microns.

Crystallite size can be influenced by several factors in the synthesis process, such as pH (amount of acid v. amount of base and timing of addition/measurement), amount of sodium, aging time of the synthesis gel, crystallization temperature, water dilution, solids content, etc. By varying these and other factors during the synthesis process, crystallite size of the germanium zeolite can be changed.

Numerous modifications and variations of the present invention are possible in light of the above teachings. It is to be understood that, within the scope of the appended claims, the invention may be practiced other than as specifically described.

What is claimed as new and desired to be secured by Letter of Patent of the United States of America is:

1. A process for converting a hydrocarbon feed containing alkanes having two to six carbon atoms per molecule to aromatics comprising contacting the hydrocarbon feed at aromatizing conditions with a catalyst to form the aromatics, wherein the catalyst comprises:
   a) a MFI zeolite having a crystallite size of less than 15 microns and
   b) platinum deposited on the zeolite
   wherein germanium is a framework element of the zeolite.

2. The process of claim 1 wherein the MFI zeolite has a crystallite size of more than about 0.2 micron.

3. The process of claim 1 wherein the MFI zeolite has a crystallite size from about 1 micron to about 7 microns.

4. The process of claim 1 wherein the MFI zeolite has a crystallite size from about 1 micron to about 4 microns.

5. The process of claim 1 wherein the MFI zeolite has a crystallite size from about 1.5 micron to about 2 microns.

6. The process of claim 1 wherein tin, lead, zirconium, titanium, vanadium, chromium, gallium, boron, indium, thallium, iron, zinc, phosphorus and combinations thereof are framework elements of the zeolite.

7. The process of claim 1 wherein platinum is present in the range of from 0.05% to 3% by weight.

8. The process of claim 1 wherein platinum is present in the range of from 0.15% to 2% by weight.

9. The process of claim 1 wherein platinum is present in the range of from 0.15% to 1.5% by weight.

10. The process of claim 1 wherein the hydrocarbon feed additionally contains sulfur.

11. A process for converting a hydrocarbon feed containing alkanes having two to six carbon atoms per molecule to aromatics comprising contacting the hydrocarbon feed at aromatizing conditions with a catalyst comprising:
    a MFI zeolite having a crystallite size of less than 15 microns platinum deposited on the zeolite and sulfur; and
    wherein germanium is a framework element of the zeolite.

12. The process of claim 1, wherein prior to contact with the feed, the catalyst is pretreated with a sulfur compound.

13. The process of claim 12 wherein the sulfur compound is $H_2S$, $C_nH_{2n+2}S$ where n=1-20, $C_nH_{2n+1}S_2$ where n=2-22 or $C_nH_{2n+1}S$ where n=2-22.

14. The process of claim 1 wherein the process is a dehydrocyclodimerization process operating at a temperature of about 350° C. to 650° C. and a pressure of about 10 to 2000 kPa gauge.

15. The process of claim 1 wherein the catalyst additionally comprises a binder selected from oxides of magnesium, aluminum, titanium, zirconium, thorium, silicon, boron or mixtures thereof.

16. The process of claim 15 wherein the binder is an oxide of silicon (silica).

17. The process of claim 1 wherein the catalyst has the formula $|H^+Pt|[Si_{91}Ge_4Al_1O_{192}]$-MFI.

18. The process of claim 1 wherein the hydrocarbon feed comprises propane.

19. The process of claim 11 wherein the amount of sulfur on the catalyst is about 10 ppm to about 0.1 weight %.

* * * * *